United States Patent
Yeh

(10) Patent No.: US 9,927,360 B2
(45) Date of Patent: Mar. 27, 2018

(54) ELECTRONIC DEVICES WITH ENVIRONMENTAL SENSORS

(71) Applicant: Apple Inc., Cupertino, CA (US)

(72) Inventor: Richard Yeh, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/250,714

(22) Filed: Aug. 29, 2016

(65) Prior Publication Data

US 2018/0059021 A1     Mar. 1, 2018

(51) Int. Cl.
| | |
|---|---|
| *G01N 21/61* | (2006.01) |
| *G01N 33/00* | (2006.01) |
| *G01N 27/16* | (2006.01) |
| *H05K 5/00* | (2006.01) |
| *G06F 1/16* | (2006.01) |

(52) U.S. Cl.
CPC ............ *G01N 21/61* (2013.01); *G01N 27/16* (2013.01); *G01N 33/004* (2013.01); *G06F 1/1616* (2013.01); *G06F 1/1626* (2013.01); *H05K 5/0017* (2013.01); *H05K 5/0086* (2013.01); *G01N 2201/061* (2013.01); *G01N 2201/068* (2013.01)

(58) Field of Classification Search
CPC ...... G01N 21/61; G01N 27/16; G01N 33/004; G06F 1/1616; G06F 1/1626; H05K 5/0017; H05K 5/0086
See application file for complete search history.

(56) References Cited

U.S. PATENT DOCUMENTS

| | | | | |
|---|---|---|---|---|
| 5,691,704 A | * | 11/1997 | Wong | G08B 17/10 340/628 |
| 8,415,626 B1 | * | 4/2013 | Wong | G01J 5/045 250/340 |

(Continued)

FOREIGN PATENT DOCUMENTS

| | | | | |
|---|---|---|---|---|
| DE | 102009050194 A1 | * | 4/2011 | ......... G01N 21/3504 |
| GB | 2464016 A | * | 4/2010 | ............. G01N 27/12 |

(Continued)

OTHER PUBLICATIONS

Kuhn et al., Investigations on a MOX Gas Sensor as an Infrared Source for an IR-based Gas Sensing System, 2012, 14th International Meeting on Chemical Sensors, pp. 233-236.*

*Primary Examiner* — Christine Sung
(74) *Attorney, Agent, or Firm* — Treyz Law Group, P.C.; Joseph F. Guihan

(57) ABSTRACT

An environmental sensor may include a heat source that heats a metal oxide sensing material. Electrodes may be formed in the metal oxide sensing material that measure the resistance of the metal oxide sensing material to determine the concentration of various gases. The environmental sensor may include an infrared light source that emits infrared light at a given wavelength. An infrared detector and bandpass filter may be used to detect the concentration of a particular gas such as carbon dioxide. In order to reduce power consumption, a heater may act as both the heat source for the metal oxide sensing material and the infrared light source for the infrared detector. The metal oxide sensing material, heater, and infrared detector may be formed in the same enclosure. The enclosure may have an opening that is aligned with an opening in an electronic device housing.

13 Claims, 14 Drawing Sheets

(56) References Cited

U.S. PATENT DOCUMENTS

| | | | |
|---|---|---|---|
| 2004/0113802 A1* | 6/2004 | Green | G01N 27/16 340/632 |
| 2004/0181346 A1* | 9/2004 | Sunshine | B82Y 15/00 702/22 |
| 2010/0050744 A1* | 3/2010 | Petrovic | G01N 21/3504 73/31.06 |
| 2012/0049071 A1 | 3/2012 | Wong | |
| 2014/0105790 A1* | 4/2014 | Gaudon | G01N 27/125 422/90 |
| 2014/0131581 A1 | 5/2014 | Lee et al. | |
| 2014/0250975 A1* | 9/2014 | Kane | G01N 1/2205 73/23.31 |

FOREIGN PATENT DOCUMENTS

| | | |
|---|---|---|
| WO | 1995022045 | 8/1995 |
| WO | 1999000659 | 1/1999 |
| WO | 2013167874 | 11/2013 |

* cited by examiner

ELECTRONIC DEVICES WITH ENVIRONMENTAL SENSORS

BACKGROUND

This relates generally to electronic devices and, more particularly, to electronic devices with environmental sensors.

Electronic devices such as cellular telephones, portable computers, and tablet computers are sometimes equipped with environmental sensors. In some situations, it may be desirable to include multiple environmental sensors in an electronic device to detect multiple environmental contaminants. However, environmental sensors may consume high amounts power and may take up valuable space within electronic devices.

It would therefore be desirable to be able to provide improved environmental sensors for electronic devices.

SUMMARY

An electronic device may be provided with electronic components such as environmental sensors.

An environmental sensor may include multiple sensor components such as a nondispersive infrared sensor and a metal oxide gas sensor. The sensor components may be mounted within an enclosure that at least partially surrounds the sensor components. The enclosure may have an opening that allows gases to enter the enclosure and interact with the sensor components.

The metal oxide gas sensor may include a heat source that heats a metal oxide sensing material. Electrodes may be formed in the metal oxide sensing material that measure the resistance of the metal oxide sensing material to determine the concentration of various gases. The nondispersive infrared sensor may include an infrared light source that emits infrared light at a given wavelength. A gas such as carbon dioxide may absorb infrared light at the given wavelength. An infrared detector and band-pass filter may therefore be used to detect how much light at the given wavelength is being absorbed to determine the concentration of a gas.

In order to reduce power consumption, a single heater may act as both the heat source for the metal oxide gas sensor and the infrared light source for the nondispersive infrared sensor. The metal oxide sensing material, heater, and infrared detector may be formed in the same enclosure of the sensor. The enclosure may have an opening that is aligned with an opening in an electronic device housing.

DETAILED DESCRIPTION

An electronic device may be provided with electronic components such as buttons, switches, displays, speakers, microphones, and environmental sensors. Environmental sensors may be provided that include multiple sensor components. A heater may be included in a sensor that acts as a heat source for a metal oxide gas sensor and an infrared light source for a nondispersive infrared sensor.

The electronic device may include one or more housing structures that form a housing for the device. The housing structures may have one or more openings. The environmental sensor may have an enclosure with an opening that is aligned with an opening in the housing structures.

Figure 1:
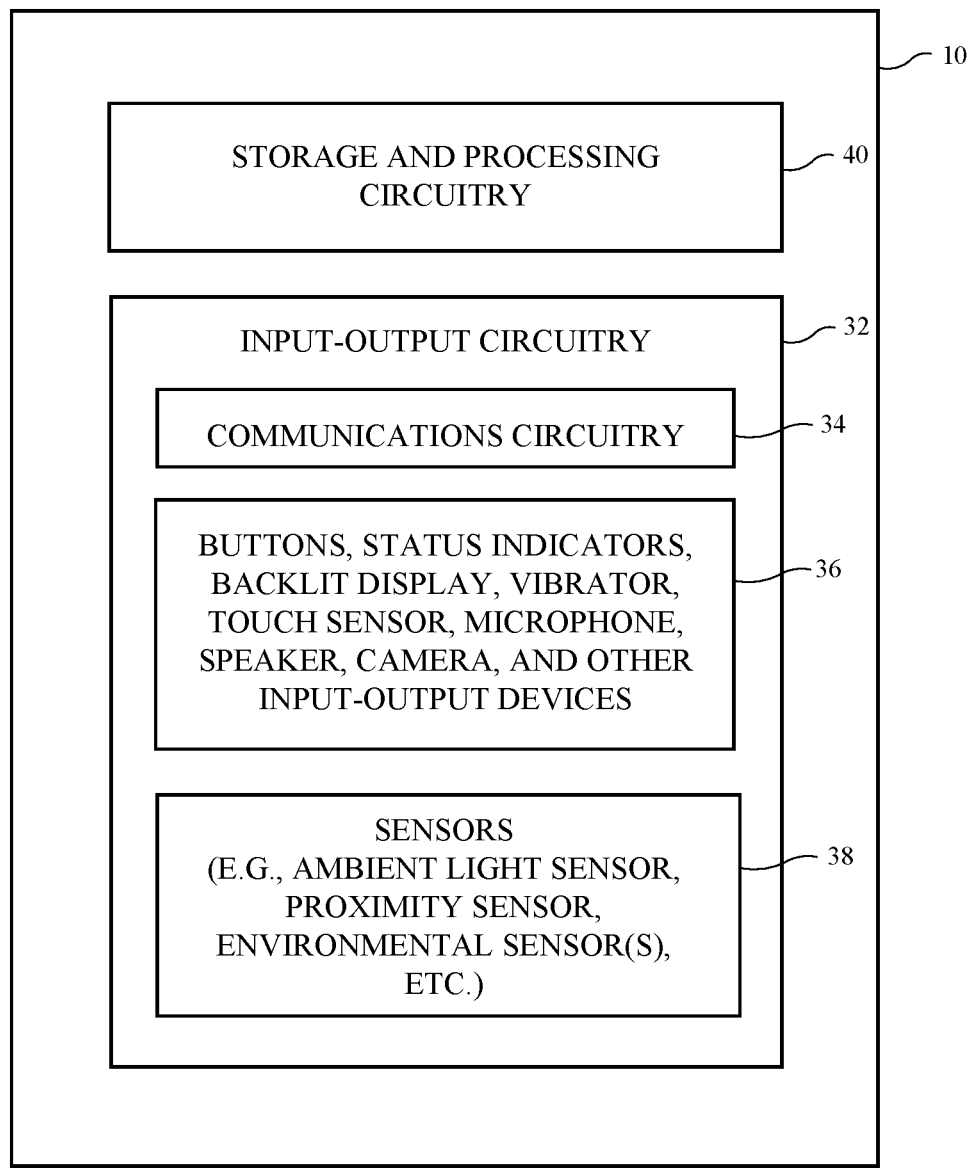
FIG. 1 is a schematic diagram of an illustrative electronic device having environmental sensors in accordance with an embodiment.
Figure 2:
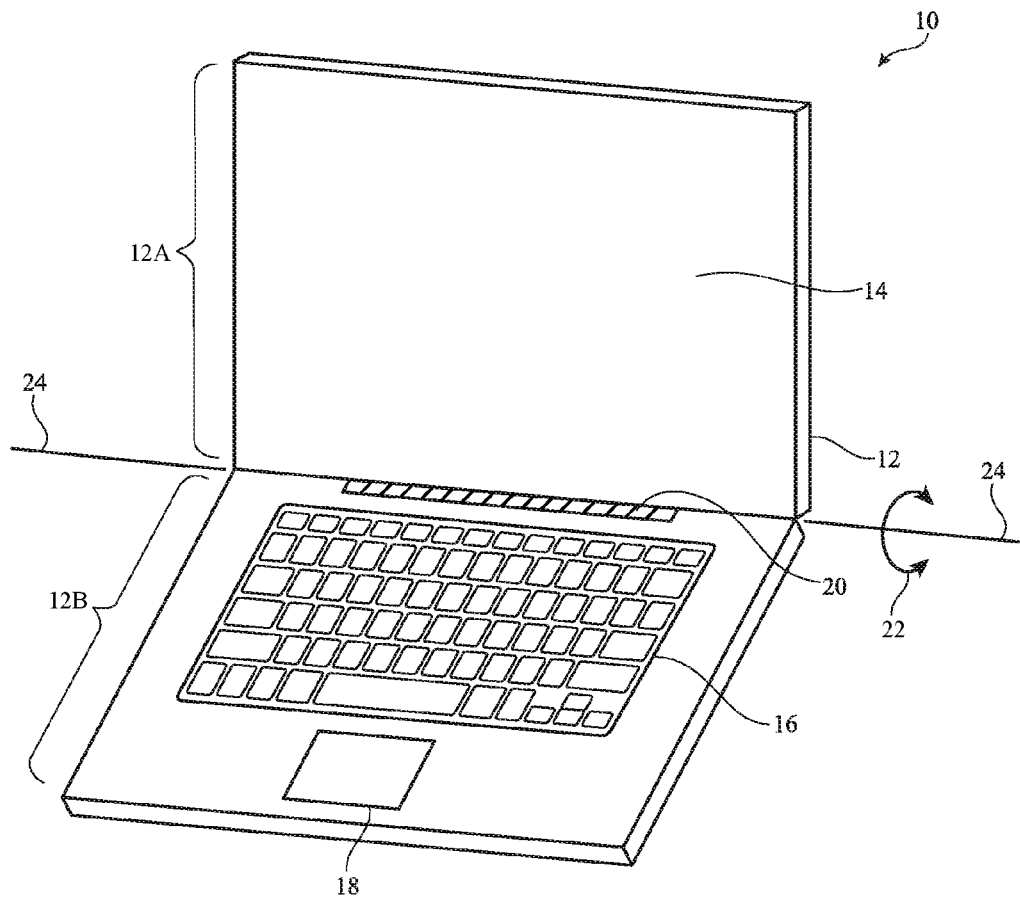
FIG. 2 is a perspective view of an illustrative electronic device such as a laptop computer of the type that may be provided with an environmental sensor in accordance with an embodiment.

A schematic diagram of an illustrative electronic device 10 showing how the device may include environmental sensors and other components is shown in FIG. 1. As shown in FIG. 1, electronic device 10 may include control circuitry such as storage and processing circuitry 40. Electronic devices such as device 10 of FIG. 1 may be cellular telephones, media players, other handheld portable devices, head-mounted devices, somewhat smaller portable devices such as wrist-watch devices, pendant devices, or other wearable or miniature devices, gaming equipment, tablet computers, notebook computers, desktop computers, televisions, computer monitors, computers integrated into computer displays, or other electronic equipment.

Storage and processing circuitry 40 may include one or more different types of storage such as hard disk drive storage, nonvolatile memory (e.g., flash memory or other electrically-programmable-read-only memory), volatile memory (e.g., static or dynamic random-access-memory), etc. Processing circuitry in storage and processing circuitry 40 may be used in controlling the operation of device 10. The processing circuitry may be based on a processor such as a microprocessor and other suitable integrated circuits. With one suitable arrangement, storage and processing circuitry 40 may be used to run software on device 10, such as internet browsing applications, email applications, media playback applications, operating system functions, software for capturing and processing images, software implementing functions associated with gathering and processing sensor data such as temperature data, software that makes adjustments to display brightness and touch sensor functionality, etc.

Input-output circuitry 32 may be used to allow data to be supplied to device 10 and to allow data to be provided from device 10 to external devices.

Input-output circuitry 32 may include wired and wireless communications circuitry 34. Communications circuitry 34 may include radio-frequency (RF) transceiver circuitry formed from one or more integrated circuits, power amplifier circuitry, low-noise input amplifiers, passive RF components, one or more antennas, and other circuitry for handling RF wireless signals. Wireless signals can also be sent using light (e.g., using infrared communications). If desired, communications circuitry 34 may be used to wirelessly transmit information from environmental sensors or other sensors within the device to external devices.

Input-output circuitry 32 may include input-output devices 36 such as buttons, joysticks, click wheels, scrolling wheels, a display, a touch screen display, other touch sensors such as track pads or touch-sensor-based buttons, vibrators, audio components such as microphones and speakers, image capture devices such as a camera module having an image sensor and a corresponding lens system, keyboards, status-indicator lights, tone generators, key pads, and other equipment for gathering input from a user or other external source and/or generating output for a user.

Input-output circuitry 32 may also include sensor circuitry. Sensor circuitry such as sensors 38 of FIG. 1 may include ambient light sensors, proximity sensors, an accelerometer, a gyroscope, environmental sensors such as non-dispersive infrared sensors and metal oxide gas sensors, sensor packages having multiple sensor components such as a pressure sensor, a temperature sensor, a humidity sensor, a gas sensor, a smoke sensor, and a microphone, and other circuitry for making measurements of the environment surrounding device 10.

In some configurations, some of input-output components 36 and some of sensors 38 may be mounted in a common sensor package having an enclosure with an opening.

Electronic devices 10 of the type shown in FIGS. 2, 3, 4, 5, and 6, and other electronic devices 10 may be provided with environmental sensors. Electronic device 10 of FIG. 2 has the shape of a laptop computer and has upper housing 12A and lower housing 12B with components such as keyboard 16 and touchpad 18. Device 10 has hinge structures 20 to allow upper housing 12A to rotate in directions 22 about rotational axis 24 relative to lower housing 12B. Display 14 is mounted in upper housing 12A. Upper housing 12A, which may sometimes referred to as a display housing or lid, is placed in a closed position by rotating upper housing 12A towards lower housing 12B about rotational axis 24. An environmental sensor may be mounted in a port that is located along the right hand edge of housing 12B (e.g., a connector port or other port) or may be located elsewhere in housing 12A or housing 12B.

Figure 3:
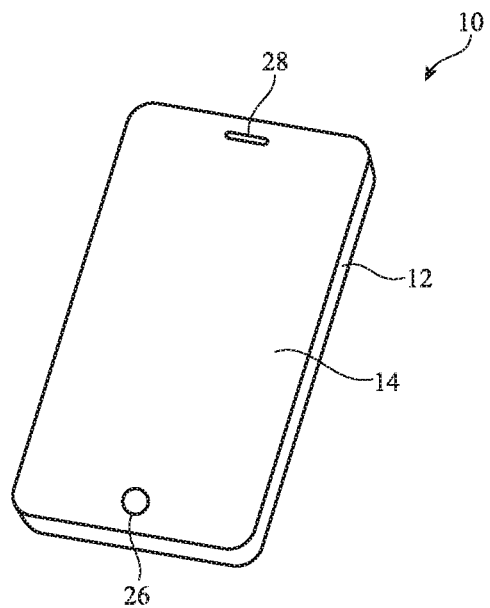
FIG. 3 is a perspective view of an illustrative electronic device such as a handheld electronic device of the type that may be provided with an environmental sensor in accordance with an embodiment.

FIG. 3 shows an illustrative configuration for electronic device 10 based on a handheld device such as a cellular telephone, music player, gaming device, navigation unit, or other compact device. In this type of configuration for device 10, housing 12 has opposing front and rear surfaces. Display 14 is mounted on a front face of housing 12. Display 14 may have an exterior layer that includes openings for components such as button 26 and speaker port 28. Environmental sensors may be located in speaker port 28 or elsewhere in device housing 12.

Figure 4:
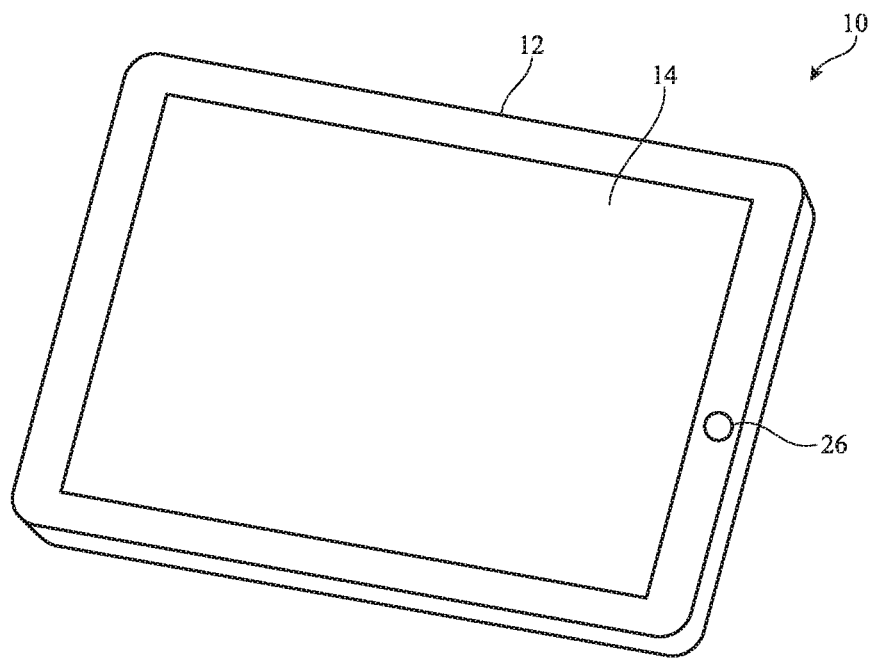
FIG. 4 is a perspective view of an illustrative electronic device such as a tablet computer of the type that may be provided with an environmental sensor in accordance with an embodiment.

In the example of FIG. 4, electronic device 10 is a tablet computer. In electronic device 10 of FIG. 4, housing 12 has opposing planar front and rear surfaces. Display 14 is mounted on the front surface of housing 12. As shown in FIG. 4, display 14 has an external layer with an opening to accommodate button 26. An environmental sensor may be mounted in electronic device 10.

Figure 5:
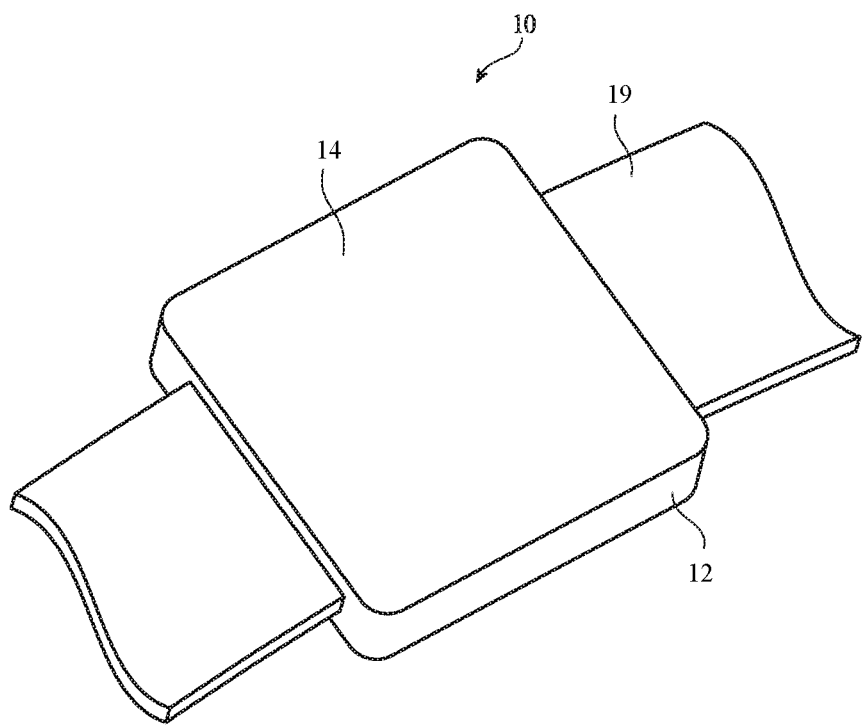
FIG. 5 is a perspective view of an illustrative wearable electronic device of the type that may be provided with an environmental sensor in accordance with an embodiment.

FIG. 5 shows an illustrative configuration for electronic device 10 in which device 10 is a wearable device such as a wristwatch device. Display 14 may be mounted on housing 12. Strap 19 may be coupled to housing 12 so that housing 12 and the rest of device 10 may be attached to the wrist or other body part of a user. Housing 12 may have openings to accommodate buttons or openings to form ports such as speaker ports or connector ports. An environmental sensor may be mounted in the ports of electronic device 10 or elsewhere in electronic device 10.

Figure 6:
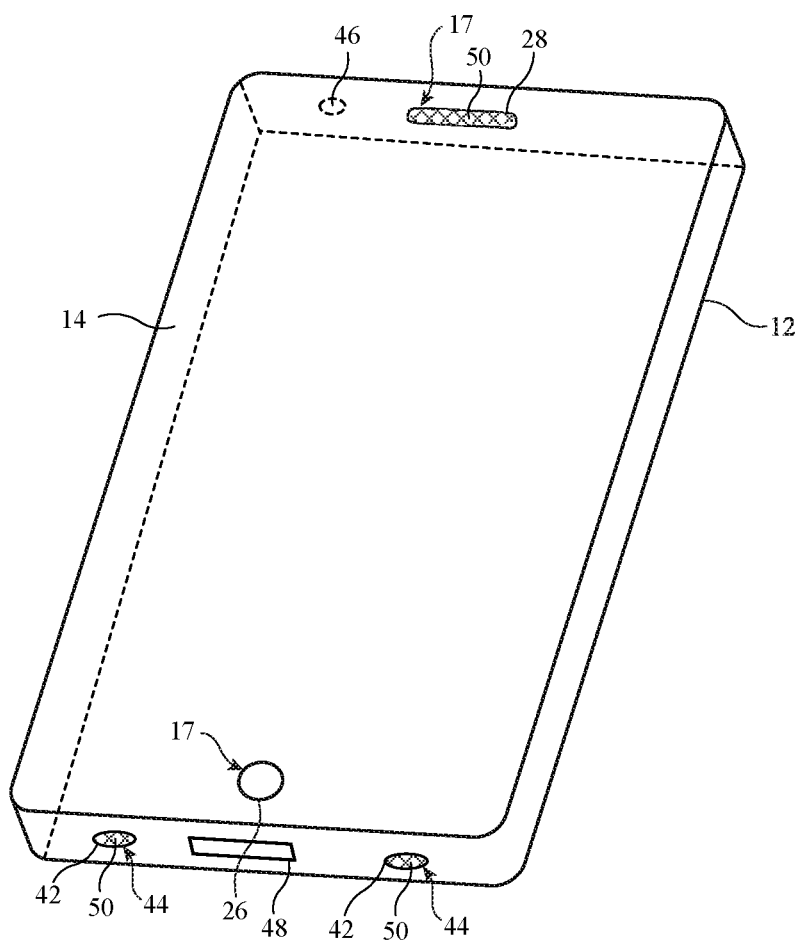
FIG. 6 is a perspective view of an illustrative electronic device having ports in accordance with an embodiment.

FIG. 6 shows an illustrative electronic device with a display such as display 14 mounted in a housing such as housing 12. Housing 12, which may sometimes be referred to as an enclosure or case, may be formed of plastic, glass, ceramics, fiber composites, metal (e.g., stainless steel, aluminum, etc.), other suitable materials, or a combination of any two or more of these materials. Housing 12 may be formed using a unibody configuration in which some or all of housing 12 is machined or molded as a single structure or may be formed using multiple structures (e.g., an internal frame structure, one or more structures that form exterior housing surfaces, etc.).

Display 14 may be a touch screen display that incorporates a layer of conductive capacitive touch sensor electrodes or other touch sensor components (e.g., resistive touch sensor components, acoustic touch sensor components, force-based touch sensor components, light-based touch sensor components, etc.) or may be a display that is not touch-sensitive. Capacitive touch screen electrodes may be formed from an array of indium tin oxide pads or other transparent conductive structures.

Device 10 may have internal user interface components such as button 26 or component 28 that occupy openings such as openings 17 in an optional rigid cover layer of display 14. Component 28 may be a speaker component or may be an environmental sensor having at least one sensor component and a speaker component. Device 10 may include additional components such as components 42 that occupy openings such as openings 44 in housing 12. Components 42 may be speaker components, microphone components, or environmental sensors having one or more sensor components. Housing 12 may be provided with additional openings such as audio port opening 46 for receiving an audio cable and connector port 48 for receiving a connector (e.g., a 30-pin connector, a universal serial bus (USB) connector, a Lightning connector, or other connector).

Openings in device 10 such as openings 44 in housing 12 and openings 17 in a rigid cover layer of display 14 may be provided with a cover member such as mesh members 50 that covers the opening while allowing air and sound to flow through openings in the mesh member.

Figure 7:
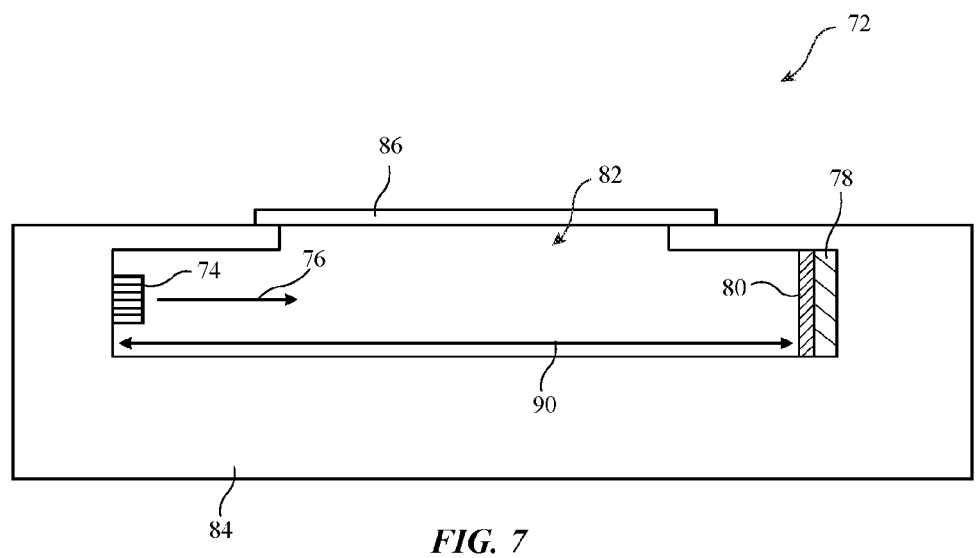
FIG. 7 is a cross-sectional side view of an illustrative nondispersive infrared sensor with an infrared light source in accordance with an embodiment.

FIG. 7 shows a cross-sectional side view of an illustrative sensor 72 that may be incorporated in electronic device 10. Sensor 72 may be a nondispersive infrared (NDIR) sensor that is used to determine the concentration of a gas in the environment. The sensor may be used to measure the concentrations of gases such as carbon dioxide ($CO_2$), methane, or any other desired gases. Sensor 72 may include an infrared light source 74 that emits infrared light 76. An infrared detector 78 and band-pass filter 80 may also be included in sensor 72. The NDIR sensor may operate by emitting broadband infrared light 76 using light source 74. Band-pass filter 80 may allow only light of a characteristic wavelength to pass through to infrared detector 78. When the gas of interest enters sensor chamber 82, infrared light at the characteristic wavelength may be absorbed by the gas. The infrared detector may therefore detect less light when the gas is present in the sensor chamber. Using this method, the amount of light detected by the infrared detector may be used to calculate the concentration of gas in the chamber.

Sensor 72 may sometimes be used to detect carbon dioxide. Carbon dioxide has an absorption peak at approximately 4.26 microns. This means that carbon dioxide gas will absorb infrared light that has a wavelength of 4.26 microns. Accordingly, light source 74 may emit infrared light 76, including infrared light with a wavelength of 4.26 microns. Band-pass filter 80 may pass light that has a wavelength of approximately 4.26 microns (i.e., 4.26±0.1 microns, 4.26±0.01 microns, etc.). Due to the presence of the band-pass filter, infrared detector 78 will detect how much light with a wavelength of 4.26 microns is being received. When no carbon dioxide is present in chamber 82, the infrared detector may have a baseline reading. When carbon dioxide is present in the chamber, the infrared detector may detect a drop in the level of light with a wavelength of 4.26 microns (since some of the light at 4.26 microns is being absorbed by the carbon dioxide). The reading of the infrared detector can therefore be used to determine the concentration of carbon dioxide in chamber 82 at any given time.

Sensor 72 may include a sensor housing 84 (sometimes referred to as an enclosure) that contains light source 74, band-pass filter 80, and infrared detector 78. Sensor housing 84 may have interior walls that form sensor chamber 82. The sensor housing may be formed from any desired material (i.e., plastic, metal, etc.). The sensor housing may have an opening that allows gas (such as carbon dioxide) to enter into the sensor chamber. The opening may be covered by filter 86. Filter 86 may keep out undesired contaminants (i.e., dust, water, etc.).

Figure 8:
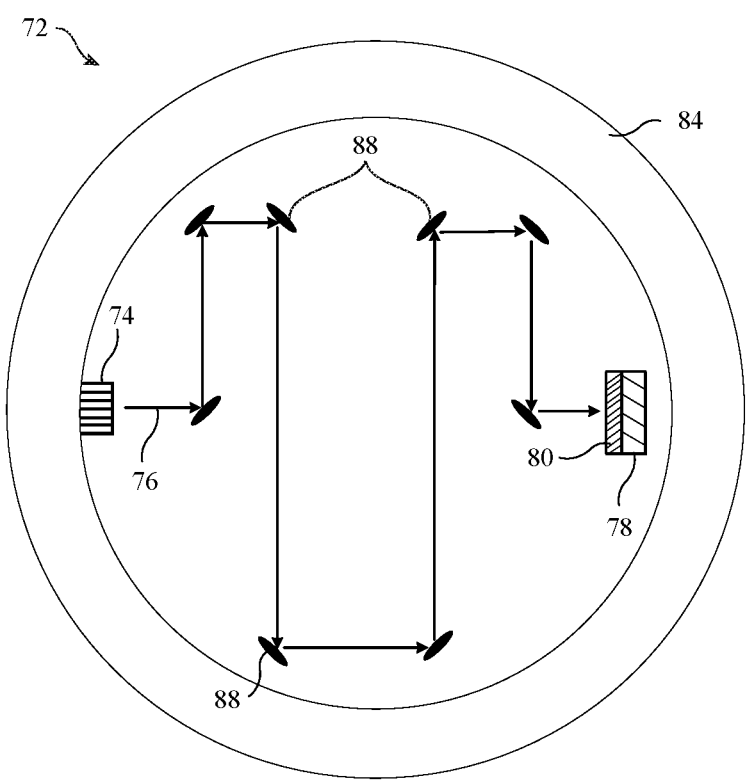
FIG. 8 is a top view of an illustrative nondispersive infrared sensor that includes reflectors to increase optical path length in accordance with an embodiment.

The sensitivity of sensor 72 may be proportional to the optical path length of the sensor. Optical path length may be considered the distance the infrared light travels from the light source to the infrared detector. FIG. 7 shows optical path length 90 between light source 74 and infrared detector 78. A longer optical path length in the sensor may result in greater sensitivity. Therefore, in order to increase the sensitivity of the NDIR sensor, the optical path length may be increased using reflectors. FIG. 8 shows a cross-sectional top view of an illustrative sensor 72 with reflectors 88 that increase the path length of the sensor. Instead of infrared light 76 from infrared light source 74 travelling directly to infrared detector 78, the light may be reflected one or more times throughout the sensor chamber of sensor 72. Reflecting the light in this way increases the optical path length of the sensor, and accordingly increases the sensitivity of the sensor.

Figure 9:
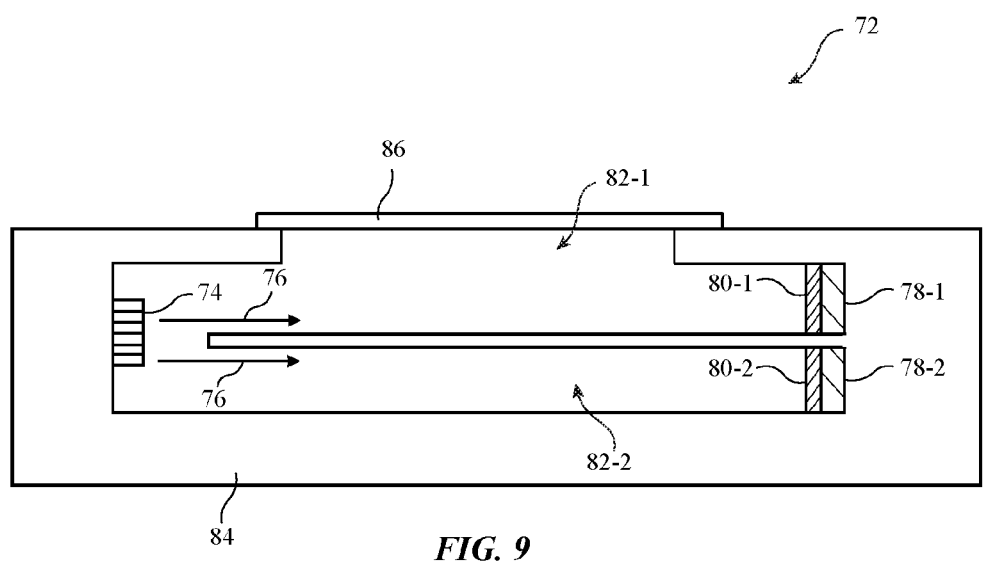
FIG. 9 is a cross-sectional side view of an illustrative nondispersive infrared sensor with two sensing chambers in accordance with an embodiment.

In order to increase the functionality of the sensor, sensor 72 may be provided with two sensing chambers, as shown in FIG. 9. Sensor 72 may still include a light source 74 that emits infrared light 76. However, some of the light may enter chamber 82-1 while some of the light may enter chamber 82-2. Each chamber may have respective band-pass filters and infrared detectors. As shown in FIG. 9, chamber 82-1 has a band-pass filter 80-1 and infrared detector 78-1. Chamber 82-2 has a band-pass filter 80-2 and infrared detector 78-2. Having two chambers may enable two different gases to be sensed by sensor 72. For example, chamber 82-1 may be used to sense a first gas and chamber 82-2 may be used to sense a second gas that is different than the first gas. The first band-pass filter 80-1 may only pass light with the characteristic wavelength of the first gas, while the second band-pass filter 80-2 may only pass light with the characteristic wavelength of the second gas. In other embodiments, the two chambers may increase the sensitivity of the sensor to a particular gas. As an example, a dual chamber carbon dioxide sensor may have a first chamber suited to detecting absorption of light at 4.26 microns. As previously discussed, carbon dioxide has an absorption peak at this wavelength. However, carbon dioxide has additional absorption peaks that can be measured. The second chamber be suited to detecting absorption of light at another wavelength associated with a carbon dioxide absorption peak (i.e., 4.50 microns). In this example, band-pass filter 80-1 in chamber 82-1 may pass light with a wavelength of approximately 4.26 microns while band-pass filter 80-2 in chamber 82-2 may pass light with a wavelength of approximately 4.50 microns. Having two chambers that produce two data points may increase the sensitivity and confidence of the sensor for a particular gas.

Figure 10:
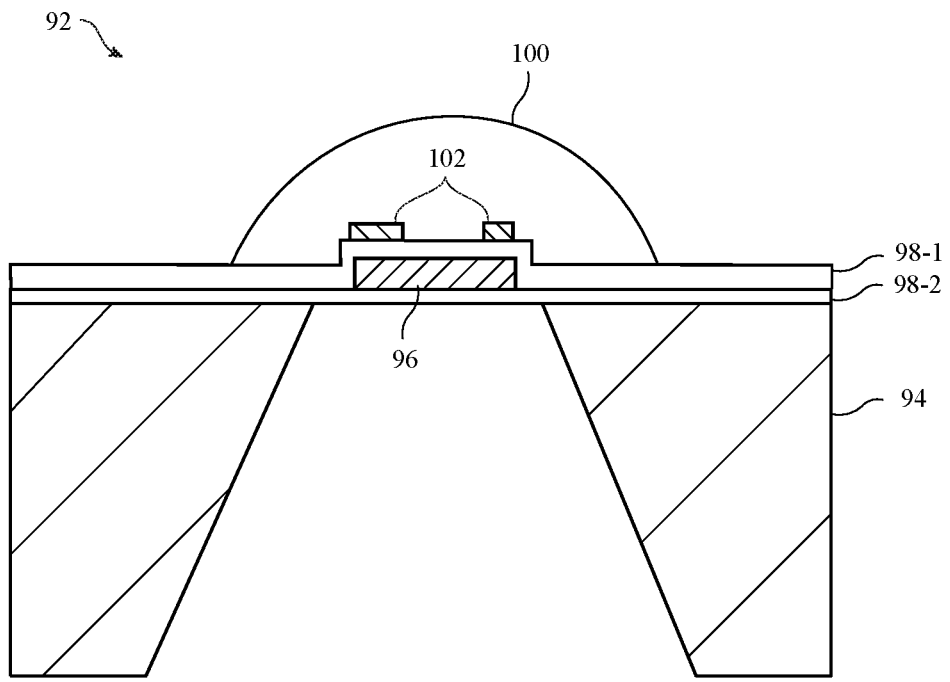
FIG. 10 is a cross-sectional side view of an illustrative metal oxide gas sensor that includes metal oxide sensing material heated by a heat source in accordance with an embodiment.

FIG. 10 shows a cross-sectional side view of another illustrative sensor that may be incorporated in electronic device 10. Sensor 92 may be a metal oxide (MOX) gas sensor that is used to determine the concentration of a gas in the environment. The sensor may be used to measure the concentrations of gases such as ozone ($O_3$), carbon monoxide (CO), nitrogen dioxide ($NO_2$), volatile organic compounds (VOCs), or any other desired gases. Metal oxide gas sensors may use a metal oxide sensing material that is heated to a temperature between 300° C. and 400° C. The metal oxide sensing material then can undergo various oxidizing or reducing reactions with gases in the environment. The resistance of the metal oxide sensing material will change as the reactions take place. By measuring the change in resistance of the metal oxide sensing material, the concentration of a gas of interest may be determined.

As shown in FIG. 10, sensor 92 may include a substrate 94. Substrate 94 may be formed from a silicon wafer or may be any other desired material. Sensor 92 may also include a heater 96 that is surrounded by layers 98-1 and 98-2. Heater 96 (sometimes referred to as a heat source) may be used to heat metal oxide sensing material 100. Metal oxide sensing material 100 may be tin dioxide or any other desired material. Heat source 96 may be capable of heating metal oxide sensing material 100 to any desired temperature (i.e., more than 30° C., more than 100° C., more than 200° C., between 300° C. and 400° C., more than 400° C., more than 500° C., less than 400° C., etc.). Layers 98-1 and 98-2 may be formed above and below heater 96. Layers 98-1 and 98-2 may be formed from any desired material (i.e., silicon nitride, silicon oxinitride, silicon oxide, etc.). Layers 98-1 and 98-2 may sometimes be referred to as membranes, insulating layers, or passivation layers. In FIG. 10, two discreet passivation layers 98-1 and 98-2 are shown. However, any number of passivation layers may be used to cover heater 96. Heater 96 may be embedded within a single passivation layer if desired. In order to measure the resistance of the metal oxide sensing material, sensor 92 may include electrodes 102. Electrodes 102 may be used to measure the resistance of the metal oxide sensing material. Any desired number of electrodes may be included in sensor 92. Electrodes 102 may be conformally covered by metal oxide sensing material 100 or embedded within metal oxide sensing material 100.

Figure 11:
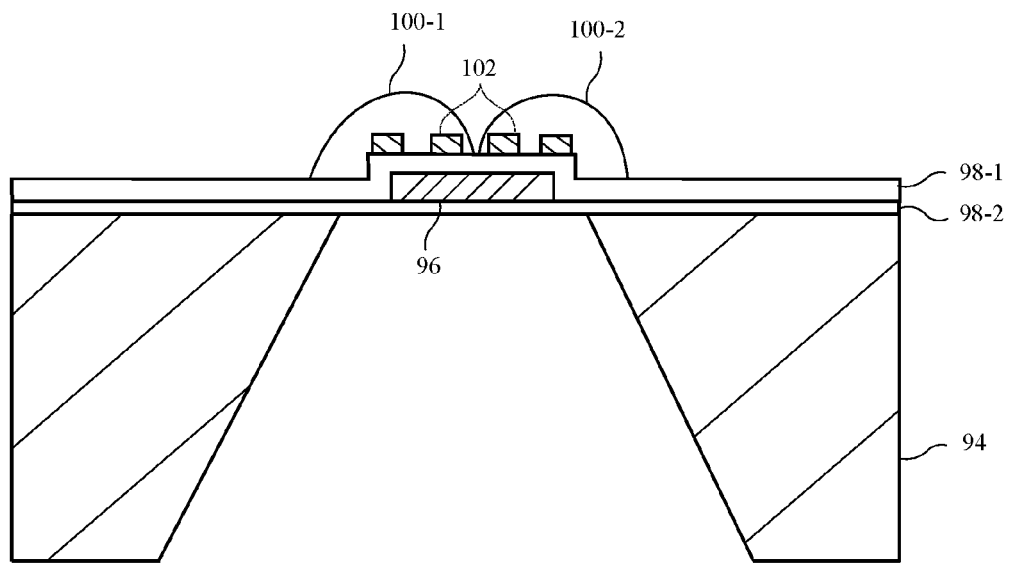
FIG. 11 is a cross-sectional side view of an illustrative metal oxide gas sensor with a single heater and two different metal oxide sensing materials in accordance with an embodiment.

If desired, sensor 92 may include a heater 96 that heats two different metal oxide sensing materials, as shown in FIG. 11. Heater 96 may heat both metal oxide sensing material 100-1 and metal oxide sensing material 100-2. Metal oxide sensing materials 100-1 and 100-2 may be different materials that are optimized to detect different gases. Each metal oxide sensing material may have one or more sets of electrodes 102 to measure the resistance of the sensing material.

Figure 12:
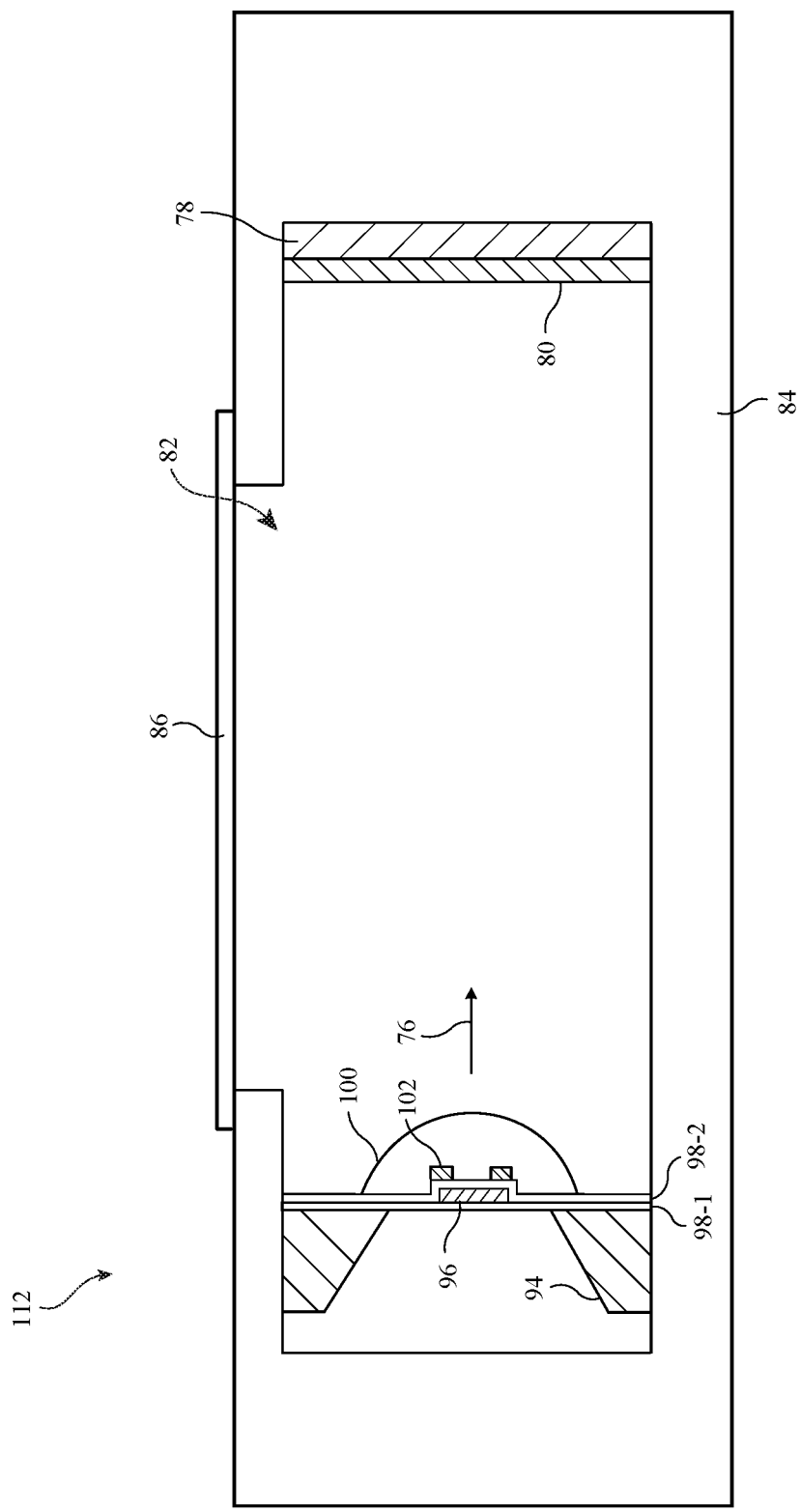
FIG. 12 is a cross-sectional side view of an illustrative sensor with a heater that acts as a heat source for a metal oxide gas sensor and an infrared light source for a nondispersive infrared sensor in accordance with an embodiment.

Both light source 74 for NDIR sensor 72 and heater 96 for MOX gas senor 92 may require significant power consumption. In certain electronic devices, it may be desirable to conserve power consumption to extend battery life. Sensor 114 in FIG. 12 reduces power consumption by using a single heat source to both heat metal oxide sensing material for a MOX gas sensor and provide infrared light for an NDIR sensor. As shown in FIG. 12, a metal oxide gas sensor with a heater 96 to heat metal oxide sensing material 100 may be provided. Layers 98-1 and 98-2 may be used to cover heater 96, and electrodes 102 may be used to measure the resistance of metal oxide sensing material 100. Substrate 94 may support these metal oxide sensing components. When heat source 96 is used to heat metal oxide sensing material 100, the heater may emit black-body radiation. Black-body radiation is electromagnetic radiation emitted by an object, and black-body radiation may include infrared light. Accordingly, when heat source 96 is heated in order to raise the temperature of metal oxide sensing layer 100, heat source 96 may emit infrared light 76. The infrared light from heater 96 may be used by band-pass filter 80 and infrared detector 78 in an NDIR sensor. If the NDIR sensor is being used to detect carbon dioxide, heater 96 may be heated to a temperature that ensures infrared light with a wavelength of 4.26 microns is emitted. By using heater 96 as both a heat source for a metal oxide gas sensor and an infrared light source for a nondispersive infrared sensor, power consumption in electronic device 10 may be conserved.

Figure 13:
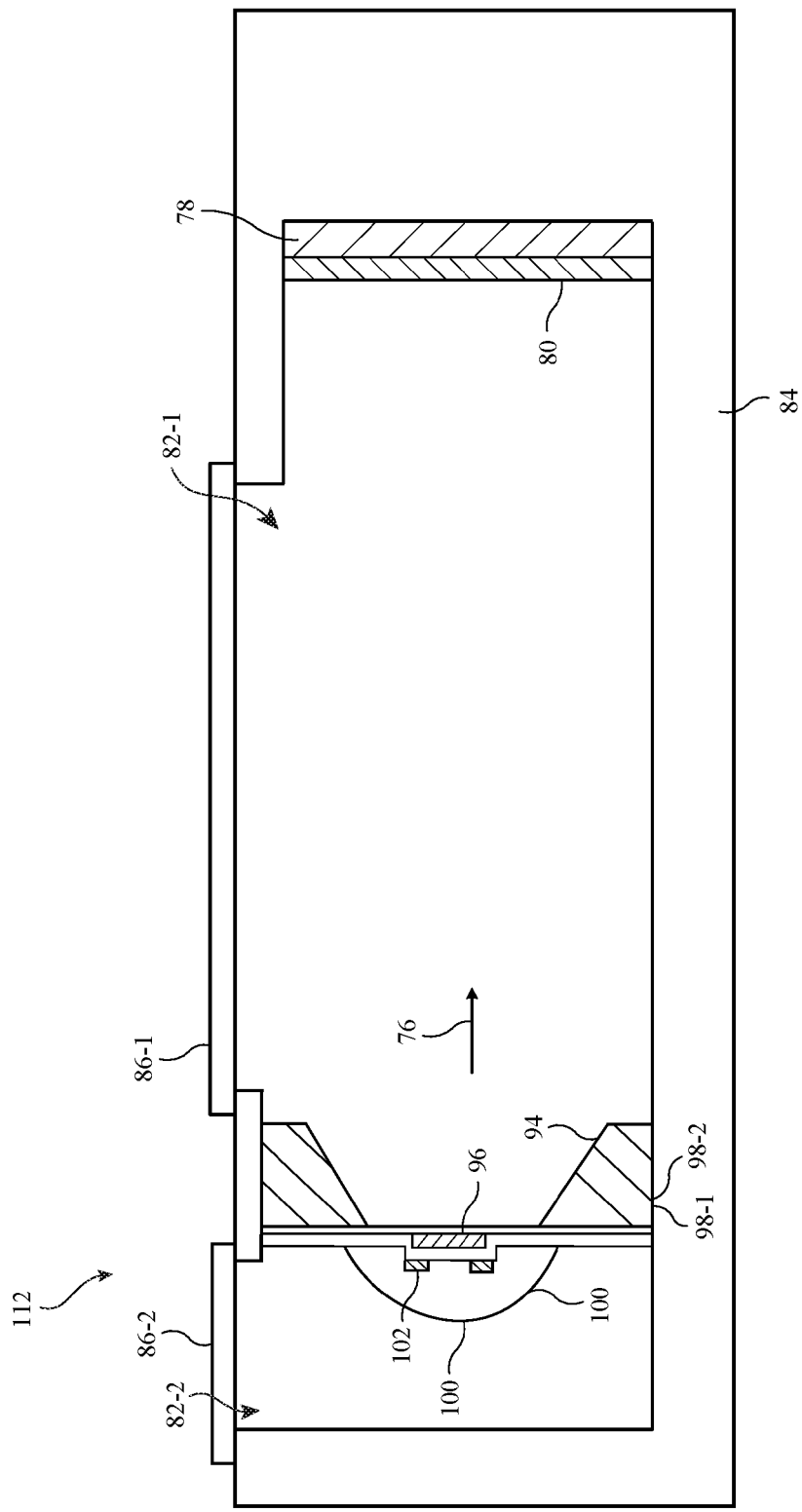
FIG. 13 is a cross-sectional side view of an illustrative sensor that has a metal oxide sensing material and infrared detector formed in different chambers of the sensor in accordance with an embodiment.

As shown in FIG. 12, metal oxide sensing layer 100 may be oriented such that the metal oxide sensing layer is facing infrared detector 78. In other words, metal oxide sensing layer 100 and infrared detector 78 may both be positioned in the same sensing chamber 82. This example is merely illustrative, and metal oxide sensing layer 100 may instead be positioned in a separate sensing chamber than infrared detector 78, as shown in FIG. 13. In sensor 112 shown in FIG. 13, heater 96 may still act as both a heat source for metal oxide sensing material 100 and as an infrared light source for infrared detector 78. Metal oxide sensing material 100 may be positioned in chamber 82-2, while infrared detector 78 may be positioned in chamber 82-1. Enclosure 84 may have an opening that allows gas to enter chamber 82-2 and a filter 86-2 that prevents contaminants from entering chamber 82-2. Enclosure 84 may also have an additional opening that allows gas to enter chamber 82-1 and a filter 86-1 that prevents contaminants from entering chamber 82-1.

The examples of possible arrangements of sensor 112 in FIGS. 12 and 13 are merely illustrative. In general, sensor 112 may have any desired arrangement that allows a single component to act as both a heat source for a metal oxide sensing layer and a light source for an NDIR sensor. In some embodiments, reflectors may be used to direct infrared light from heater 96 to infrared detector 78. This may enable the infrared light emitted from both sides of heater 96 to be directed to infrared detector 78, increasing the sensitivity of the NDIR sensor. Reflectors may also lengthen the optical path length of the NDIR sensor, which increases the sensitivity of the NDIR sensor.

Figure 14:
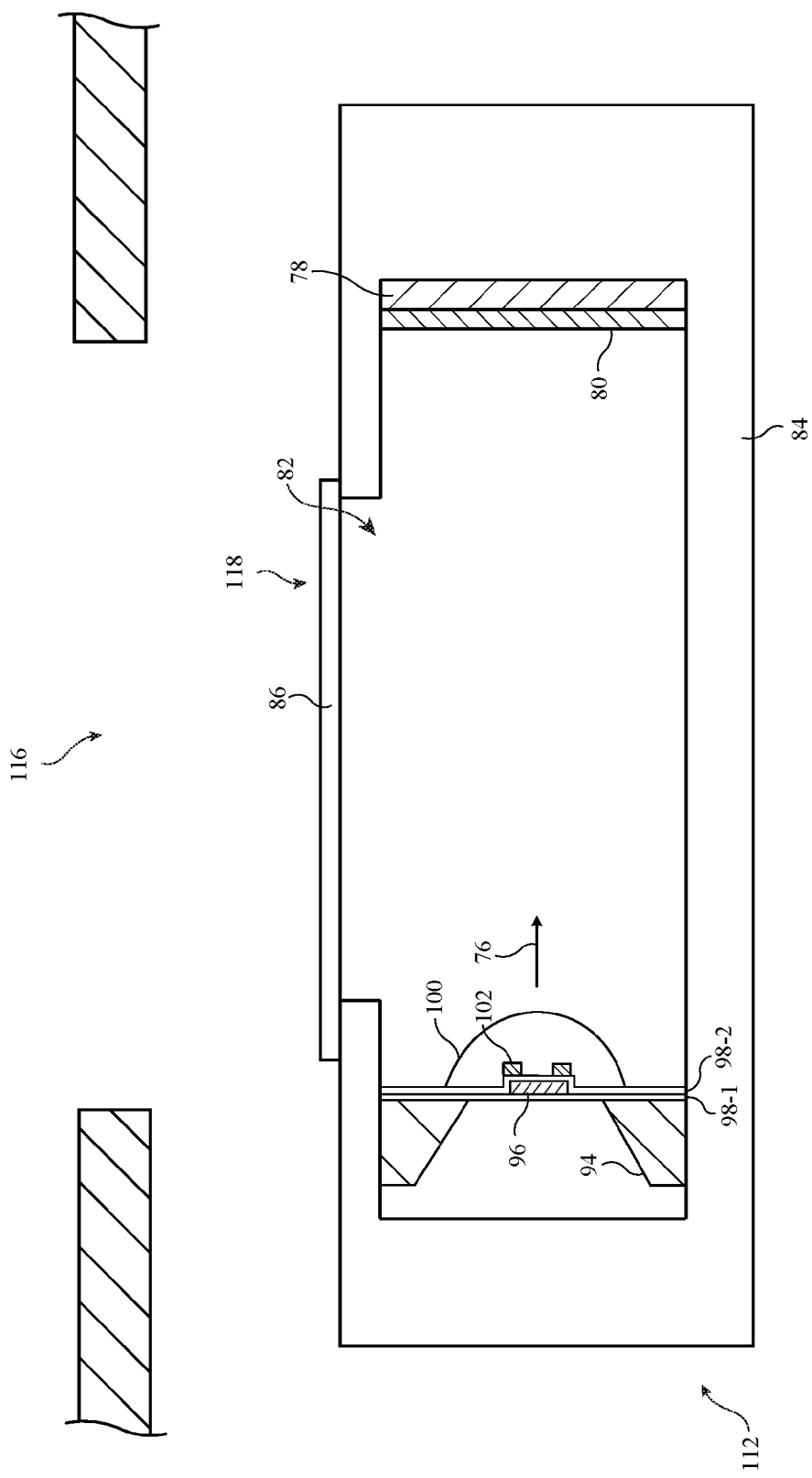
FIG. 14 is a cross-sectional side view of an illustrative electronic device with a sensor that is aligned with an opening in an electronic device structure in accordance with an embodiment.

Sensor 112 may be positioned in electronic device 10 in a number of different ways. As shown in FIG. 14, electronic device 10 may include a sensor such as sensor 112 aligned with an opening in the electronic device. Electronic device structure 114 may have an opening 116 that allows gases from the exterior of the device to enter sensing chamber 82. In other words, gases may pass through opening 116 and filter 86 to reach sensing chamber 82. Enclosure 84 may have an opening 118 that is covered by the filter. As shown in FIG. 14, opening 118 in sensor housing 84 may be aligned with opening 116 in electronic device structure 114.

Electronic device structure 114 may be any desired component in electronic device 10. For example, electronic device structure 114 may be the housing of the electronic device (i.e., housing 12 in FIG. 6), and opening 116 may be an opening in the housing (i.e., openings 44 or 46 in FIG. 6). Opening 116 may alternatively be an opening in a display cover glass in the electronic device. Opening 116 may also accommodate other components in the electronic device such as button components, speaker components, or microphone components. Opening 116 may be an audio port opening for receiving an audio cable or a connector port opening for receiving a connector (e.g., a 30-pin connector, a universal serial bus (USB) connector, a Lightning connector, or other connector). Opening 116 in device 10 may be provided with a cover member such as a mesh member (i.e., mesh 50) that covers the opening while allowing air and sound to flow through openings in the mesh member.

Figure 15:
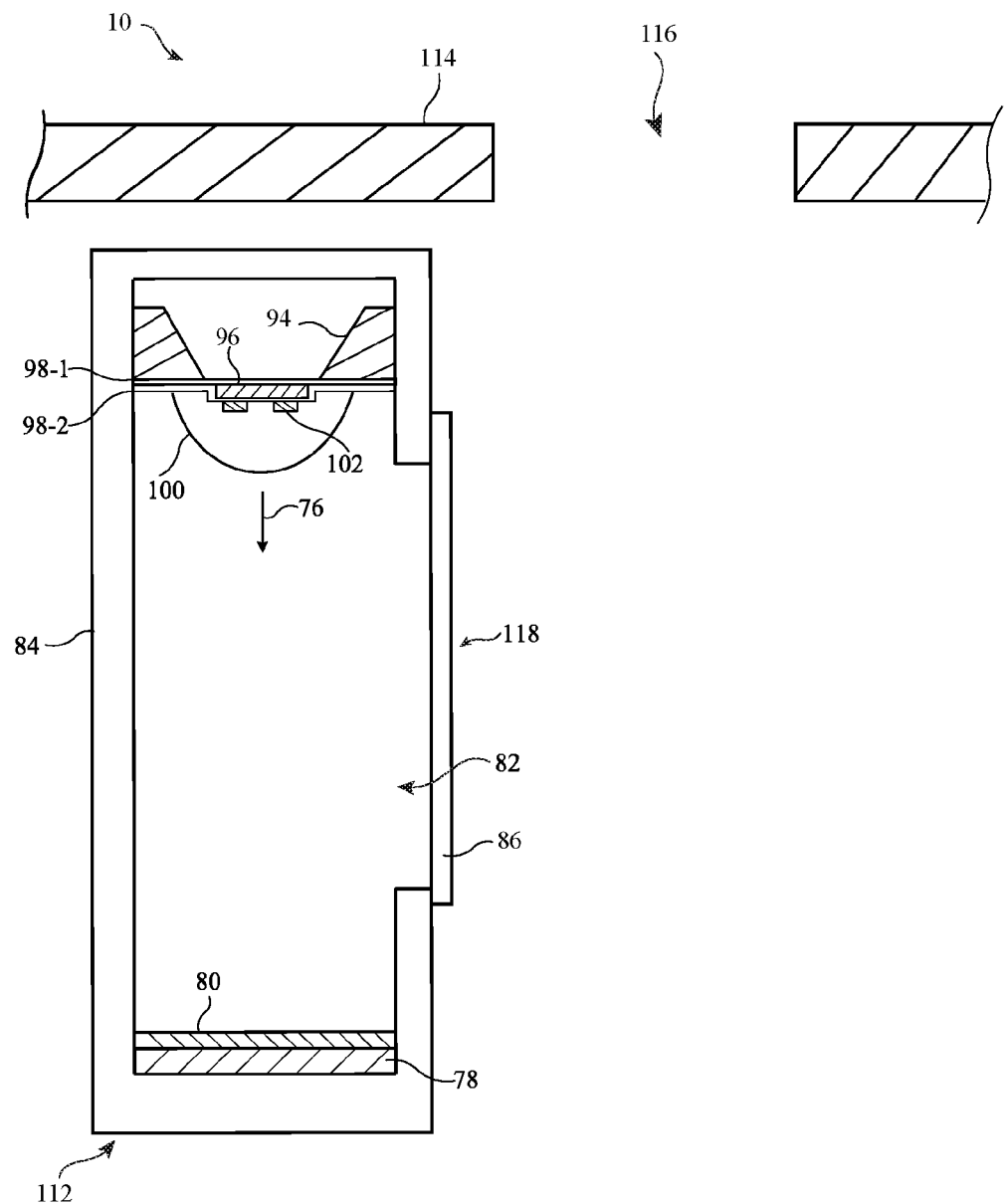
FIG. 15 is a cross-sectional side view of an illustrative electronic device with a sensor that is not directly aligned with an opening in an electronic device structure in accordance with an embodiment.

In an alternate arrangement, sensor 112 may be positioned in the interior of electronic device 10 but may not be directly aligned with an opening in the electronic device. An arrangement of this type is shown in FIG. 15. As shown in FIG. 15, sensor 112 may be positioned in the interior of electronic device 10. An opening 116 in electronic device housing structure 114 may allow gas from the exterior of the device to enter the interior of the device and sensor 112. Sensor 112 may have an opening 118 in sensor housing 84 that allows gas to enter sensor chamber 86. However, as shown in FIG. 15 opening 118 does not need to be directly aligned with opening 116. Openings 116 and 118 may be non-overlapping. Openings 116 and 118 may be formed in respective planes. The plane of opening 116 may be perpendicular to the plane of opening 118 (as shown in FIG. 15), parallel to the plane of opening 118 (as shown in FIG. 14), or formed at another desired angle relative to the plane of opening 118.

The foregoing is merely illustrative and various modifications can be made by those skilled in the art without departing from the scope and spirit of the described embodi-

What is claimed is:

1. A sensor comprising:
   a housing enclosure with a first opening that allows gas to enter a first chamber and a second opening that allows gas to enter a second chamber;
   a heater;
   a metal oxide sensing material in the first chamber that is heated by the heater;
   electrodes in the metal oxide sensing material that measure a resistance of the metal oxide sensing material to determine a concentration of at least a first gas;
   a substrate that supports the metal oxide sensing material and the electrodes, wherein the substrate is interposed between the first and second chambers and wherein the substrate at least partially defines the first and second chambers; and
   an infrared detector in the second chamber that is configured to detect infrared light emitted by the heater to determine a concentration of at least a second gas, wherein the heater is interposed between the metal oxide sensing material and the infrared detector.

2. The sensor defined in claim 1, wherein the first opening is covered by a first filter and the second opening is covered by a second filter.

3. The sensor defined in claim 1, further comprising:
   a band-pass filter that is interposed between the heater and the infrared detector.

4. The sensor defined in claim 3, wherein the heater is configured to emit infrared light of a given wavelength while heating the metal oxide sensing material, and wherein the band-pass filter is configured to only pass infrared light of the given wavelength to the infrared detector.

5. The sensor defined in claim 1, wherein the second gas comprises carbon dioxide.

6. A sensor comprising:
   an enclosure with first and second chambers;
   a metal oxide sensing material in the first chamber of the enclosure;
   electrodes in the metal oxide sensing material that are configured to measure a resistance of the metal oxide sensing material;
   a substrate that supports the metal oxide sensing material and the electrodes, wherein the substrate is interposed between the first and second chambers and wherein the substrate at least partially defines the first and second chambers;
   an infrared light detector in the second chamber of the enclosure;
   a band-pass filter adjacent to the infrared light detector that only allows infrared light of a given wavelength to reach the infrared light detector; and
   a heater interposed between the electrodes and the infrared light detector that both heats the metal oxide sensing material and emits the infrared light at the given wavelength that is detected by the infrared light detector.

7. The sensor defined in claim 6, wherein the given wavelength is 4.26 microns and the sensor is configured to determine a concentration of carbon dioxide in the enclosure.

8. The sensor defined in claim 6, further comprising a passivation layer interposed between the heater and the metal oxide sensing material.

9. The sensor defined in claim 6, further comprising at least one reflector in the enclosure that reflects the infrared light at the given wavelength from the heater to the infrared light detector.

10. An electronic device comprising:
    a housing with an exterior and an interior;
    a display within the housing; and
    an environmental sensor within the interior of the housing, wherein the environmental sensor includes an enclosure, a metal oxide gas sensor that detects gas in a first chamber of the enclosure, a nondispersive infrared sensor that detects gas in a second chamber of the enclosure, wherein the metal oxide gas sensor includes a heat source, wherein the nondispersive infrared sensor includes an infrared light source, wherein a heater in the environmental sensor acts as both the heat source for the metal oxide gas sensor and the infrared light source for the nondispersive infrared sensor, wherein the heater is configured to heat a metal oxide sensing material for the metal oxide gas sensor, wherein the heater is configured to emit infrared light that is detected by an infrared light detector in the nondispersive infrared sensor, wherein the heater is interposed between the metal oxide sensing material and the infrared light detector, wherein the housing has an opening that allows air from the exterior to reach the first and second chambers of the environmental sensor, wherein the environmental sensor comprises a substrate that supports the metal oxide sensing material, wherein the substrate is interposed between the first and second chambers, and wherein the substrate at least partially defines the first and second chambers.

11. The electronic device defined in claim 10, wherein the environmental sensor comprises an enclosure, and wherein the heater, the metal oxide sensing material, and the infrared light detector are formed in the enclosure.

12. The electronic device defined in claim 11, wherein the enclosure has first and second openings that are aligned with the opening in the housing.

13. The electronic device defined in claim 12, wherein the nondispersive infrared sensor is configured to determine a concentration of carbon dioxide in the enclosure.

* * * * *